US 8,328,713 B2

(12) United States Patent
Ishihara (10) Patent No.: US 8,328,713 B2
(45) Date of Patent: Dec. 11, 2012

(54) CAPSULE MEDICAL DEVICE, METHOD FOR OPERATING THE SAME, AND CAPSULE MEDICAL DEVICE SYSTEM

(75) Inventor: Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 223 days.

(21) Appl. No.: 12/868,239

(22) Filed: Aug. 25, 2010

(65) Prior Publication Data
US 2010/0324371 A1    Dec. 23, 2010

Related U.S. Application Data (63) Continuation of application No. PCT/JP2009/055045, filed on Mar. 16, 2009.

(30) Foreign Application Priority Data

Mar. 24, 2008   (JP) ................................. 2008-076337

(51) Int. Cl.
*A61B 1/04* (2006.01)
(52) U.S. Cl. ......................... 600/118; 600/117; 600/103
(58) Field of Classification Search .................. 600/109, 600/103, 160, 117, 118, 476
See application file for complete search history.

(56) References Cited

U.S. PATENT DOCUMENTS

| 7,083,579 | B2 * | 8/2006 | Yokoi et al. ................... 600/593 |
| 7,118,529 | B2 * | 10/2006 | Glukhovsky et al. .......... 600/160 |
| 7,653,429 | B2 * | 1/2010 | Madar et al. ................... 600/476 |
| 2002/0177779 | A1 * | 11/2002 | Adler et al. .................... 600/476 |
| 2003/0117491 | A1 * | 6/2003 | Avni et al. ....................... 348/77 |
| 2005/0054897 | A1 * | 3/2005 | Hashimoto et al. ............ 600/118 |
| 2005/0148847 | A1 |  7/2005 | Uchiyama et al. |
| 2006/0155174 | A1 * | 7/2006 | Glukhovsky et al. .......... 600/301 |
| 2006/0189843 | A1 * | 8/2006 | Nakamura et al. ............. 600/118 |
| 2007/0066868 | A1 |  3/2007 | Shikii |
| 2009/0118583 | A1 * | 5/2009 | Matsumoto .................... 600/118 |
| 2009/0124853 | A1 * | 5/2009 | Gono et al. .................... 600/109 |
| 2009/0208071 | A1 |  8/2009 | Nishimura et al. |
| 2010/0137686 | A1 * | 6/2010 | Meron et al. ................... 600/118 |

FOREIGN PATENT DOCUMENTS

| JP | 2002-345739 | 12/2002 |
| JP | 2003-38424 | 2/2003 |
| JP | 2005-080694 | 3/2005 |
| JP | 2005-334331 | 12/2005 |
| JP | 2006-223377 | 8/2006 |
| JP | 2007-82664 | 4/2007 |
| WO | WO 2004054430 A2 * | 7/2004 |

OTHER PUBLICATIONS

International Search Report dated Jun. 30, 2009.

* cited by examiner

*Primary Examiner* — John P Leubecker
(74) *Attorney, Agent, or Firm* — Scully, Scott, Murphy & Presser, P.C.

(57) ABSTRACT

The required minimum amount of examination site information is acquired, stored, or transmitted without missing an affected area, thus reducing power consumption, reducing the size of a battery disposed in a capsule, and reducing the size of a casing. Provided is a capsule medical device including a casing having a capsule shape; a light-detecting section, disposed in the casing, for detecting information about the intensity of light from outside the casing; an information-acquiring section for acquiring examination site information from an examination site positioned outside the casing; and a determination section for determining whether or not to acquire, store, or transmit, to the outside, the examination site information acquired by the information-acquiring section on the basis of the information about the intensity of the light detected by the light-detecting section.

12 Claims, 11 Drawing Sheets

CAPSULE MEDICAL DEVICE, METHOD FOR OPERATING THE SAME, AND CAPSULE MEDICAL DEVICE SYSTEM

CROSS REFERENCE TO RELATED APPLICATIONS

This is a continuation of International Application PCT/JP/2009/055045, with an international filing date of Mar. 16, 2009, which is hereby incorporated by reference herein in its entirety. This application claims the benefit of Japanese Patent Application No. 2008-076337, the content of which is incorporated herein by reference.

BACKGROUND OF THE INVENTION

1. Field of the Invention

The present invention relates to capsule medical devices, methods for operating the devices, and capsule medical device systems.

2. Description of Related Art

In the related art, there is a known capsule medical device that has a casing having a capsule shape, that is introduced into a patient's body, and that takes an image of the interior of a body cavity to acquire image information (see, for example, Japanese Unexamined Patent Application, Publication No. 2003-38424).

This capsule medical device includes wireless transmission means to transmit the acquired image information toward an external device disposed outside the patient's body.

Because the capsule medical device of Japanese Unexamined Patent Application, Publication No. 2003-38424 acquires image information in the body cavity at predetermined time intervals, it needs to acquire a large amount of image information at an increased frame rate to carry out examination over the entire length of the inner wall of the body cavity in the longitudinal direction without missing an affected area. If high-resolution image information is to be acquired, the amount of data thereof is enormous, and accordingly the amount of power required to transmit the data to a memory for storing the data or to the outside is increased, thus the size of the battery and the size of the casing of the capsule medical device tend to be increased.

BRIEF SUMMARY OF THE INVENTION

A capsule medical device, a method for operating the device, and a capsule medical device system capable of acquiring, storing, or transmitting the required minimum amount of examination site information without missing an affected area, thus reducing power consumption, reducing the size of the battery disposed in the capsule, and reducing the size of the casing is provided.

A first aspect of the present invention is a capsule medical device including a casing having a capsule shape; a light-detecting section, disposed in the casing, for detecting information about the intensity of light from outside the casing; an information-acquiring section for acquiring examination site information from an examination site positioned outside the casing; and a determination section for determining whether or not to acquire, store, or transmit, to the outside, the examination site information acquired by the information-acquiring section on the basis of the information about the intensity of the light detected by the light-detecting section.

According to the above first aspect, after the casing having a capsule shape is introduced into a body cavity, the light-detecting section disposed in the casing detects information about the intensity of light from outside the casing. The determination section then determines whether or not to acquire, store, or transmit, to the outside, examination site information on the basis of the information about the intensity of the detected light. Because the acquisition of the information about the intensity of the light, which is a smaller amount of information, does not require a large amount of power, the need for acquiring, storing, or transmitting, to the outside, the examination site information can be accurately determined with a small amount of power. This avoids the disadvantage of wastefully acquiring, storing, or transmitting, to the outside, the examination site information, which is a larger amount of information, thus preventing battery exhaustion, reducing the size of the battery, and reducing the size of the casing.

In the above first aspect, the examination site information may be image information from the examination site positioned outside the casing.

Because the acquisition of image information requires a large amount of power, battery exhaustion can be effectively suppressed by avoiding acquisition of unnecessary image information.

In the above first aspect, additionally, the examination site information may be brightness information from the examination site positioned outside the casing.

By doing so, the amount of examination site information can be reduced to reduce the amount of power required for acquisition, storage, and transmission, thus effectively avoiding battery exhaustion.

In the above first aspect, additionally, the determination section may be configured to determine that the examination site information is to be acquired, stored, or transmitted to the outside if the information about the intensity of the light detected by the light-detecting section exceeds a predetermined threshold.

By doing so, if the information about the intensity of the light is lower than the predetermined threshold, it is possible to avoid wasteful processing such as acquiring examination site information that is dark, thus having a small amount of information, or where no diseased area is present, or storing or transmitting, to the outside, such examination site information. This consequently prevents battery exhaustion.

In the above configuration, additionally, an examination-site identifying section for identifying the examination site and a threshold-changing section for changing the threshold depending on the type of examination site identified by the examination-site identifying section may be provided.

By doing so, the determination section can determine whether or not to acquire, store, or transmit, to the outside, the examination site information with respect to the threshold depending on the type of examination site. This avoids acquisition etc. of unnecessary information and therefore prevents battery exhaustion more effectively than uniform determination with respect to a single threshold because the examination site information can be acquired etc. depending on the type of examination site.

In the above configuration, additionally, the examination-site identifying section may include an examination-time measuring section for measuring examination time and an examination-site storing section storing types of examination sites in association with the examination time, and a type of examination site stored in the examination-site storing section may be specified on the basis of the examination time measured by the examination-time measuring section.

By doing so, the type of examination site stored in the examination-site storing section can be specified on the basis of the examination time measured by the examination-time measuring section to easily select the threshold depending on the type of examination site and accurately determine whether or not to acquire, store, or transmit, to the outside, the examination site information In the above first aspect, additionally, the light-detecting section may split the light from outside the casing to detect information about the intensities of the individual split components, and the determination section may execute the determination on the basis of the ratio of the information about the intensities of the individual split components detected by the light-detecting section.

By doing so, it can be accurately determined whether or not an important site such as a diseased area is present at the examination site under examination on the basis of the information about the intensities of the individual split components of the light emitted from the examination site.

In the above first aspect, additionally, the light-detecting section and the information-acquiring section may be constituted by a common light-intensity detecting device.

By doing so, the configuration can be simplified.

In the above configuration, additionally, the light-intensity detecting device may be an image-acquisition device having a plurality of pixels, the light-detecting section may detect the information about the intensity of the light from at least some of the pixels of the image-acquisition device, and the information-acquiring section may acquire an image of the examination site from at least some of the pixels of the image-acquisition device.

By doing so, the information about the intensity of the light can be easily detected using information from some of the pixels of the image-acquisition device capable of image acquisition, thus simplifying the configuration.

In the above configuration, additionally, the determination section may execute the determination on the basis of an average value of information about the intensities of pixels having light intensity information exceeding a predetermined threshold and the number of the pixels.

By doing so, it can be accurately determined whether or not an important site such as a diseased area is present at the examination site under examination using the average value of the information about the intensities of the pixels and the number of the pixels as criteria.

In the above first aspect, additionally, an agent-elapsed-time measuring section for measuring elapsed time from administration of an agent to a patient and a threshold-changing section for changing the threshold on the basis of the elapsed time measured by the agent-elapsed-time measuring section may be provided.

By doing so, it can be more accurately determined whether or not to acquire, store, or transmit, to the outside, the examination site information by taking into account the temporal change of the light emitted from the agent.

In addition, a second aspect of the present invention is a method for operating a capsule medical device that has a casing having a capsule shape and that is introduced into a patient's body, and the method includes a light-intensity detecting step of detecting information about the intensity of light from outside the casing; a determination step of determining whether or not to acquire examination site information from an examination site positioned outside the casing on the basis of the information about the intensity of the light detected in the light-intensity detecting step; and an information-acquiring step of acquiring the examination site information on the basis of a result of the determination in the determination step.

According to the above second aspect, because it is determined in the determination step whether or not to acquire examination site information from the examination site on the basis of the information about the intensity of the light detected in the light-intensity detecting step, it is possible to avoid the disadvantage of acquiring unnecessary examination site information in the information-acquiring step, thus preventing battery exhaustion and permitting examination over an extended period of time.

In addition, a third aspect of the present invention is a method for operating a capsule medical device that has a casing having a capsule shape and that is introduced into a patient's body, and the method includes a light-intensity detecting step of detecting information about the intensity of light from outside the casing; an information-acquiring step of acquiring examination site information from an examination site positioned outside the casing; a determination step of determining whether or not to store or transmit, to the outside, the examination site information acquired in the information-acquiring step on the basis of the information about the intensity of the light detected in the light-intensity detecting step; and an information-processing step of storing or transmitting the examination site information on the basis of a result of the determination in the determination step.

According to the above third aspect, because it is determined in the determination step whether or not to store or transmit, to the outside, the examination site information acquired in the information-acquiring step on the basis of the information about the intensity of the light detected in the light-intensity detecting step, it is possible to avoid the disadvantage of storing or transmitting, to the outside, unnecessary examination site information in the information-processing step, thus preventing battery exhaustion and permitting examination over an extended period of time.

In addition, a fourth aspect of the present invention is a capsule medical device system including the above capsule medical device and an external device disposed outside the capsule medical device; the external device includes an examination-site identifying section for identifying, from outside the patient's body, the examination site where the capsule medical device is positioned and a transmitting section for transmitting threshold information corresponding to the examination site identified by the examination-site identifying section; the capsule medical device includes a receiving section for receiving the threshold information transmitted from the transmitting section; and the determination section determines that the examination site information is to be acquired, stored, or transmitted to the outside if the information about the intensity of the light detected by the light-detecting section exceeds a threshold corresponding to the threshold information received by the receiving section.

According to the above fourth aspect, the examination-site identifying section disposed in the external device identifies, from outside the patient's body, the examination site where the capsule medical device is positioned, and the transmitting section transmits the threshold information corresponding to the identified examination site to the capsule medical device. This allows the capsule medical device to determine whether or not to acquire, store, or transmit, to the outside, the examination site information on the basis of the threshold transmitted from the external device without the need for storing thresholds in association with types of examination sites.

The present invention provides the advantage of acquiring, storing, or transmitting the required minimum amount of examination site information without missing an affected area, thus reducing power consumption, reducing the size of the battery disposed in the capsule, and reducing the size of the casing.

DETAILED DESCRIPTION OF THE INVENTION

A capsule medical device 1 and a method for operating the device 1 according to an embodiment of the present invention will be described below with reference to FIGS. 1 to 3.

Figure 1:
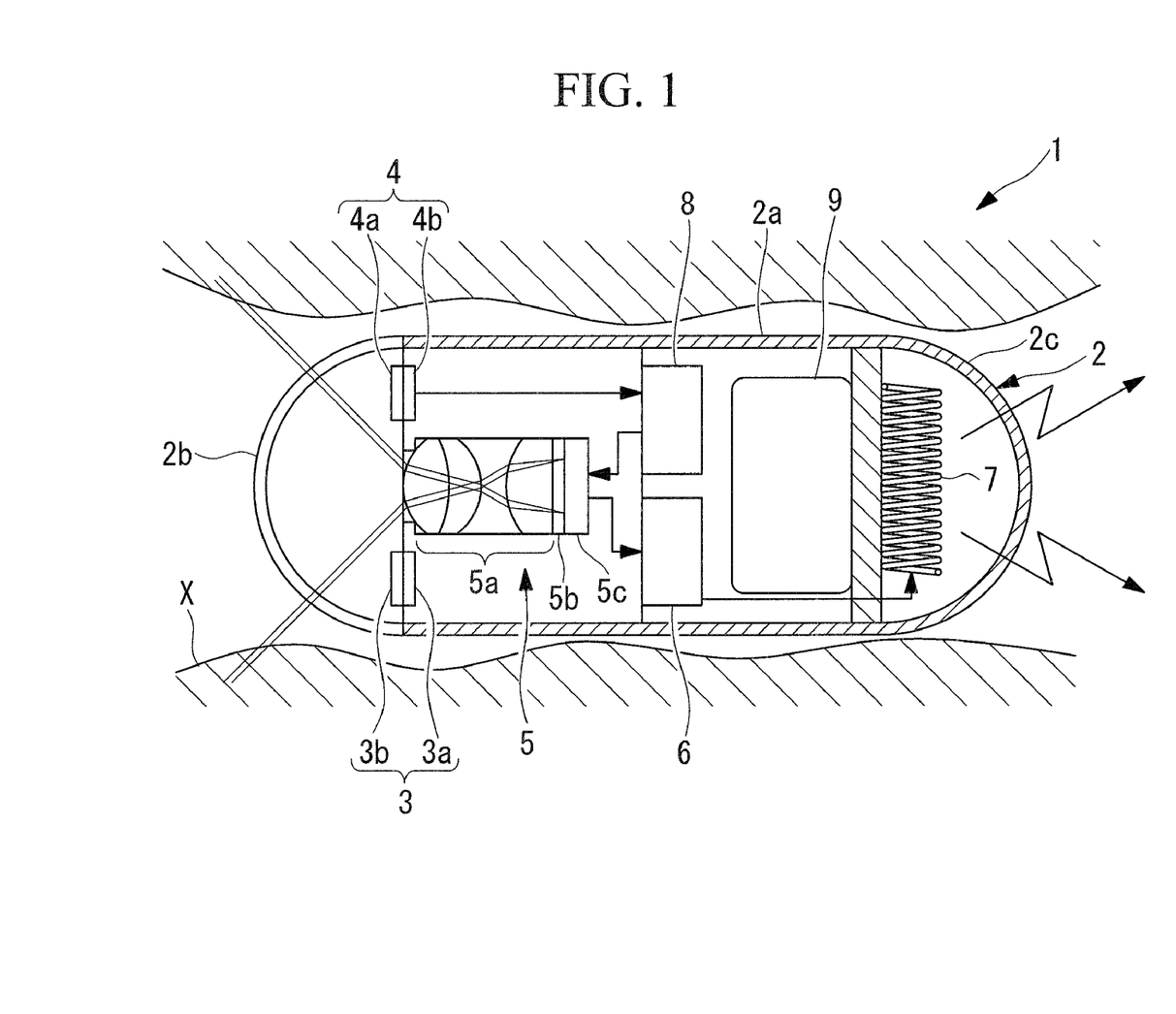
FIG. 1 is a longitudinal sectional view showing a capsule medical device according to an embodiment of the present invention.

As shown in FIG. 1, the capsule medical device 1 according to this embodiment includes a casing 2 having a capsule shape in which the two ends of a cylindrical casing body 2a are respectively sealed by a hemispherical transparent window 2b and end plate 2c, an illumination section 3 accommodated in the casing 2 and emitting excitation light through the transparent window 2b, a light-detecting section 4 for detecting fluorescence entering the casing 2 through the transparent window 2b from an examination site outside the casing 2, an image-acquiring section (information-acquiring section) 5 for taking an image of the examination site, an image-generating section 6 for generating image information (examination site information) on the basis of a two-dimensional luminance distribution acquired by the image-acquiring section 5, an antenna (transmitting section) 7 for wirelessly transmitting the generated image information outside the casing 2, a control section (determination section) 8 for controlling these, and a battery 9 for supplying power to the individual sections. Wiring from the battery 9 to the individual sections is not shown.

The illumination section 3 includes, for example, an LED 3a for emitting wideband light and an excitation light filter 3b for transmitting, of the light emitted from the LED 3a, only light at the excitation wavelength, so that it exits through the transparent window 2b.

The light-detecting section 4 includes an excitation light cut filter 4a for blocking excitation light and a photodetector 4b for detecting the intensity of fluorescence from which the excitation light is removed.

The image-acquiring section 5 includes an image-acquisition optical system 5a for collecting fluorescence entering the casing 2 through the transparent window 2b, an excitation light cut filter 5b for blocking excitation light in the collected fluorescence, and an image-acquisition device 5c, such as a high-sensitivity CCD, for acquiring the two-dimensional intensity distribution of the fluorescence from which the excitation light is removed.

Figure 2:
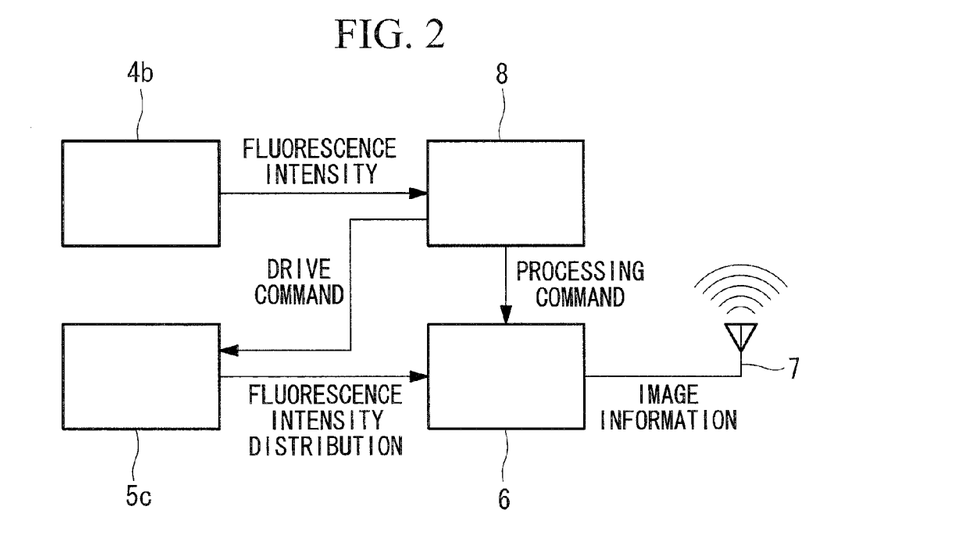
FIG. 2 is a block diagram showing the internal structure of the capsule medical device in FIG. 1.
Figure 3:
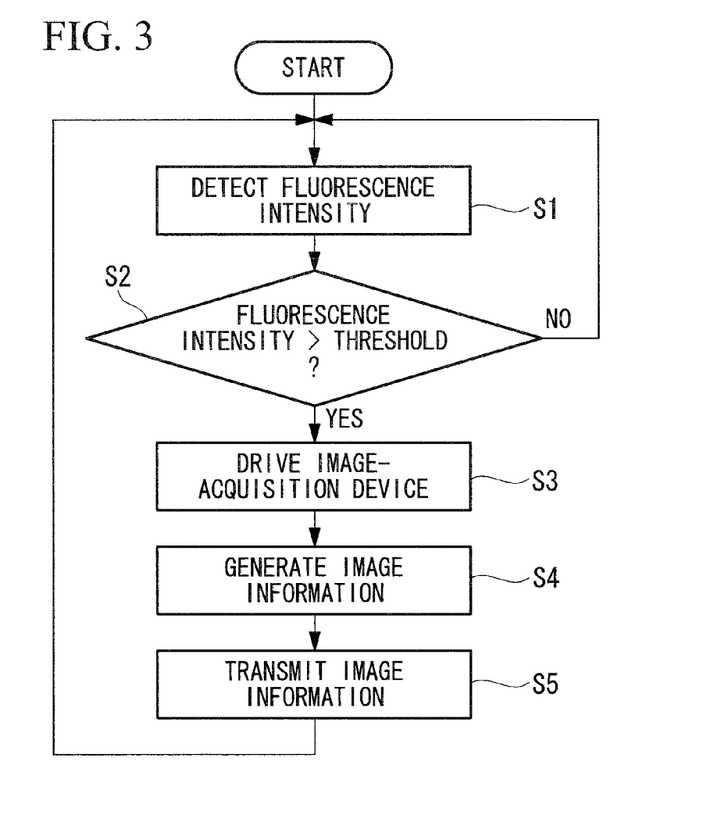
FIG. 3 is a flowchart showing a method for operating the capsule medical device in FIG. 1.

As shown in FIG. 2, the control section 8 is connected to the photodetector 4b, fluorescence intensity information transmitted from the photodetector 4b with a predetermined threshold stored in the control section 8 in advance, and, if the fluorescence intensity is higher than the threshold, determines that the image-acquisition device 5c is to be driven to acquire a fluorescence intensity distribution by outputting a drive command signal to the image-acquisition device 5c.

In addition, the control section 8 causes the image-generating section 6 to generate image information from the fluorescence intensity distribution acquired by the image-acquisition device 5c and wirelessly transmits the image information via the antenna 7 outside the casing 2.

The method for operating the thus-configured capsule medical device 1 according to this embodiment will now be described.

With the capsule medical device 1 according to this embodiment introduced into a patient's body cavity X, the illumination section 3 is operated to irradiate an examination site with excitation light through the transparent window 2b to excite a fluorescent substance present at the examination site so that it emits fluorescence, which then enters the casing 2 through the transparent window 2b.

The fluorescence emitted from the fluorescent substance is, for example, fluorescence emitted from a dye that is introduced into the patient by, for example, spraying, intravenous injection, or oral administration in advance before the administration of the capsule medical device 1 to the patient and that is accumulated at the examination site, or autofluorescence emitted from the examination site itself.

The intensity of the fluorescence entering the casing 2 is detected by the light-detecting section 4 (light-intensity detecting step S1). The control section 8 then determines whether or not to drive the image-acquisition device 5c on the basis of information about the intensity of the detected fluorescence (determination step S2). The determination is made by the control section 8 on the basis of whether or not the luminance of the fluorescence detected by the light-detecting section 4 exceeds a predetermined threshold.

If the fluorescence intensity exceeds the threshold, it can be determined that a large amount of fluorescent substance is present at the examination site. The fluorescence intensity detected is often high where a diseased area is present because a certain fluorescent agent accumulates specifically at a diseased area such as cancer. Accordingly, if the fluorescence intensity is higher than the predetermined threshold, the image-acquisition device 5c can be driven (information-acquiring step S3) to acquire image information at an examination site where a diseased area is probably present. Subsequently, image information is generated by the image-generating section 6 (image-information generating step S4) and is wirelessly transmitted (image-information transmitting step S5).

Thus, the capsule medical device 1 according to this embodiment acquires and wirelessly transmits an image only when the fluorescence intensity exceeds a predetermined threshold. This provides the advantage of avoiding acquisition and wireless transmission of unnecessary images with small amounts of information, such as blank images, thus preventing exhaustion of the battery 9. This allows a reduction in the sizes of the battery 9 and the casing 2.

In addition, the amount of image information required to be transmitted outside can be minimized to reduce the amount of image information to be checked later. This provides the advantage of facilitating diagnosis.

In addition, an examination site with high fluorescence intensity can be more reliably selected because the photodetector 4b generally has higher sensitivity than a CCD.

Although the control section 8 determines whether or not to drive the image-acquisition device 5c on the basis of the fluorescence intensity detected by the light-detecting section 4 in this embodiment, it may instead determine whether or not to wirelessly transmit the generated image information. Because wireless transmission requires a larger amount of power than other processing, exhaustion of the battery 9 can be effectively prevented merely by avoiding wireless transmission of unnecessary image information.

Figure 4:
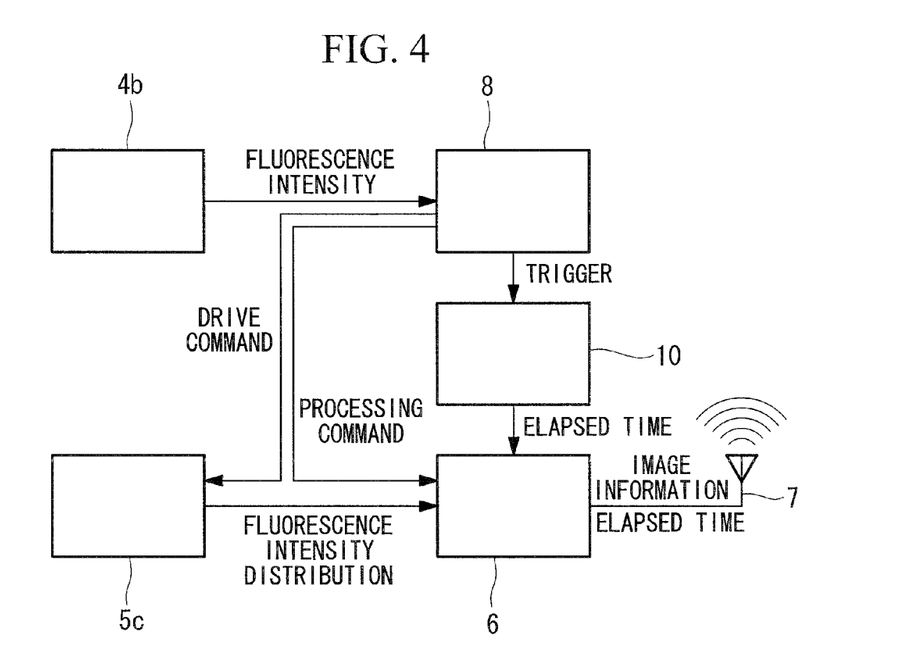
FIG. 4 is a block diagram showing a first modification of the capsule medical device in FIG. 1.

In this embodiment, additionally, as shown in FIG. 4, a timer (examination-time measuring section) 10 for measuring examination time (for example, the elapsed time from introduction into the body cavity) may be provided in the casing 2 and, if the fluorescence intensity detected by the light-detecting section 4 is higher than a predetermined threshold, the control section 8 may wirelessly transmit information about the examination time measured by the timer 10 outside the casing 2 in association with the image information generated by the image-generating section 6. By measuring the examination time, the examination site, such as an organ, shown in the image information can be easily located.

In this case, although the image information acquired by the image-acquisition device 5c is associated with examination time in this embodiment, fluorescence intensity information may instead be associated with examination time by replacing the image-acquisition device 5c with a photodetector. Because the examination site can be located using examination time, the presence of, for example, the presence a diseased area can be checked merely on the basis of fluorescence intensity information serving as examination site information.

In this case, additionally, the configuration can be simplified by the shared use of the photodetector 4b for detecting the fluorescence intensity for determining whether or not to acquire examination site information as the photodetector for detecting the fluorescence intensity serving as examination site information. This is also advantageous in that the amount of data is small because the fluorescence intensity information acquired by the photodetector 4b contains no two-dimensional position information, thus demanding a smaller amount of power for acquisition and wireless transmission and a shorter processing time.

In addition, a CCD may be shared instead of sharing the photodetector 4b. In this case, the fluorescence intensity used for determining whether or not to take an image with the image-acquisition device 5c may be the maximum or average value of the fluorescence intensities of the individual pixels acquired by the CCD.

Figure 5:
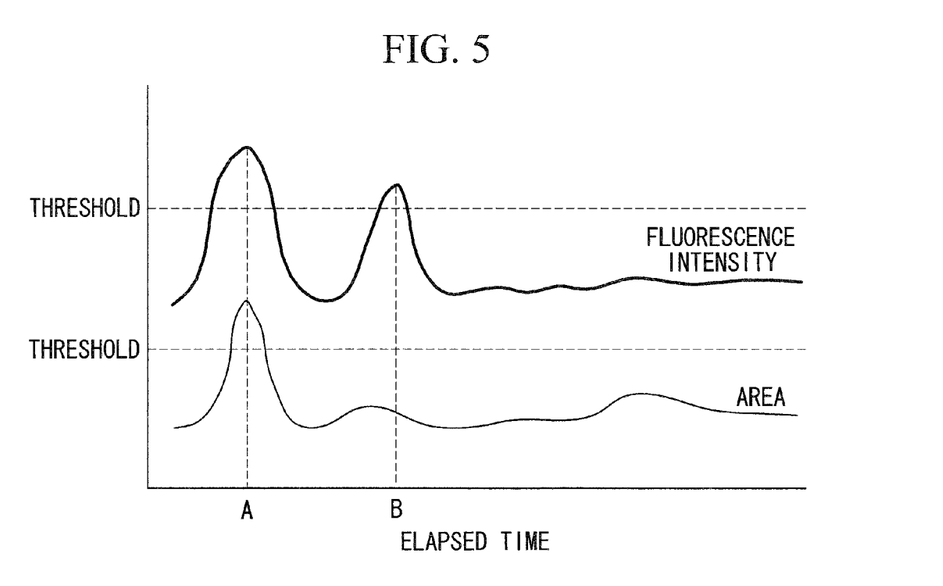
FIG. 5 is a graph showing an example of a determination method for a second modification of the capsule medical device in FIG. 1.

In this case, in addition to the maximum or average value of the fluorescence intensities of the individual pixels, the area of a region where the fluorescence intensity is at or above a predetermined threshold (that is, the number of pixels having such fluorescence intensities) may be used to determine whether or not to take an image with the image-acquisition device 5c. By doing so, as shown in FIG. 5, it is possible to prevent acquisition, due to noise, of an image of an examination site having a relatively narrow area and a high fluorescence intensity (reference B in FIG. 5), thus more reliably acquiring an image of an examination site that is suspected of being diseased (reference A in FIG. 5).

Figure 6:
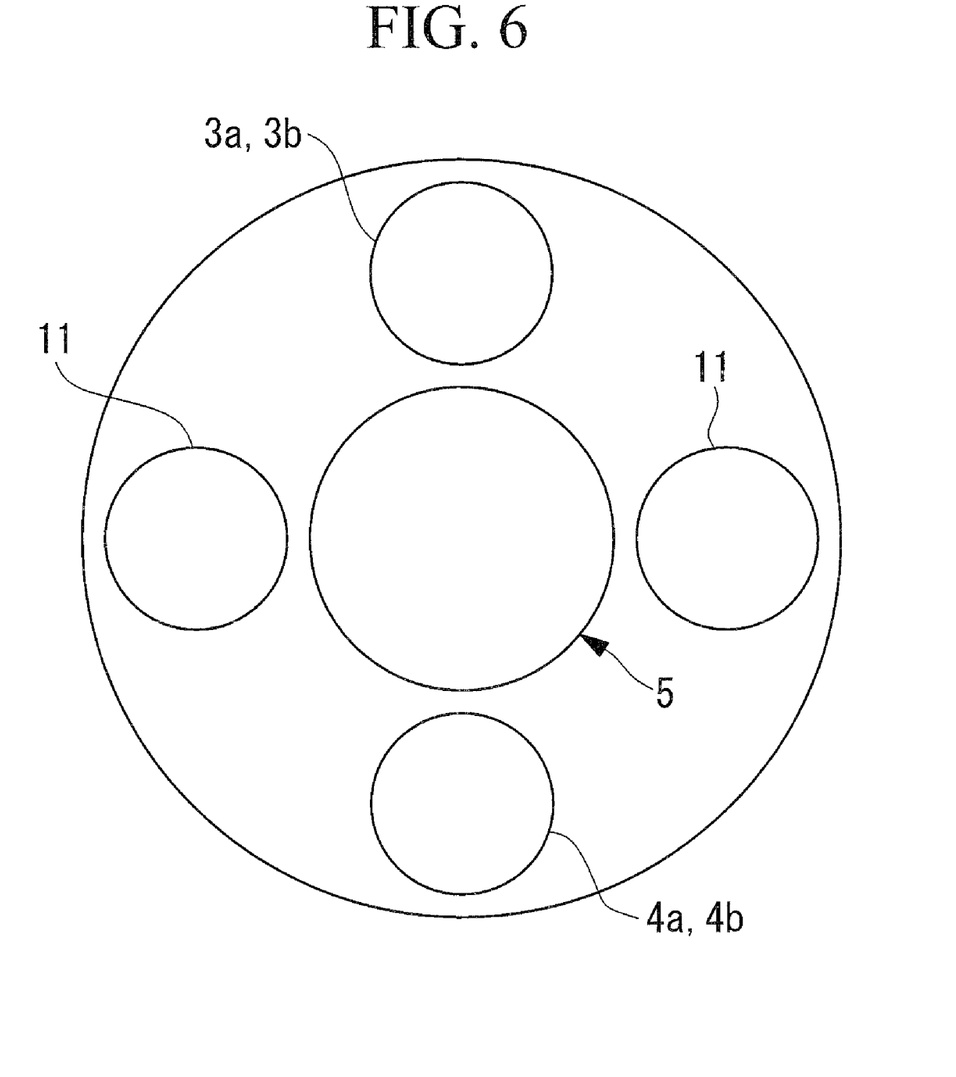
FIG. 6 is a front view showing an arrangement of LEDs and a photodiode in a third modification of the capsule medical device in FIG. 1.

In addition, although a fluorescent image is acquired on the basis of the fluorescence intensity detected by the photodetector 4b in this embodiment, as shown in FIG. 6, it is instead possible to provide white light LEDs 11 having no excitation filter 3b and to acquire a two-dimensional white light image by detecting light reflected from the examination site by the image-acquisition device 5c. In this case, the excitation light cut filter 5b does not have to be provided in front of the image-acquisition device 5c if the LED 3a having the excitation filter 3b emits excitation light for detection of fluorescence intensity by the photodetector 4b and the light LEDs 11 having no excitation filter 3b are illuminated, whereas the LED 3a having the excitation filter 3b is switched off, for acquisition of a white light image.

Figure 7:
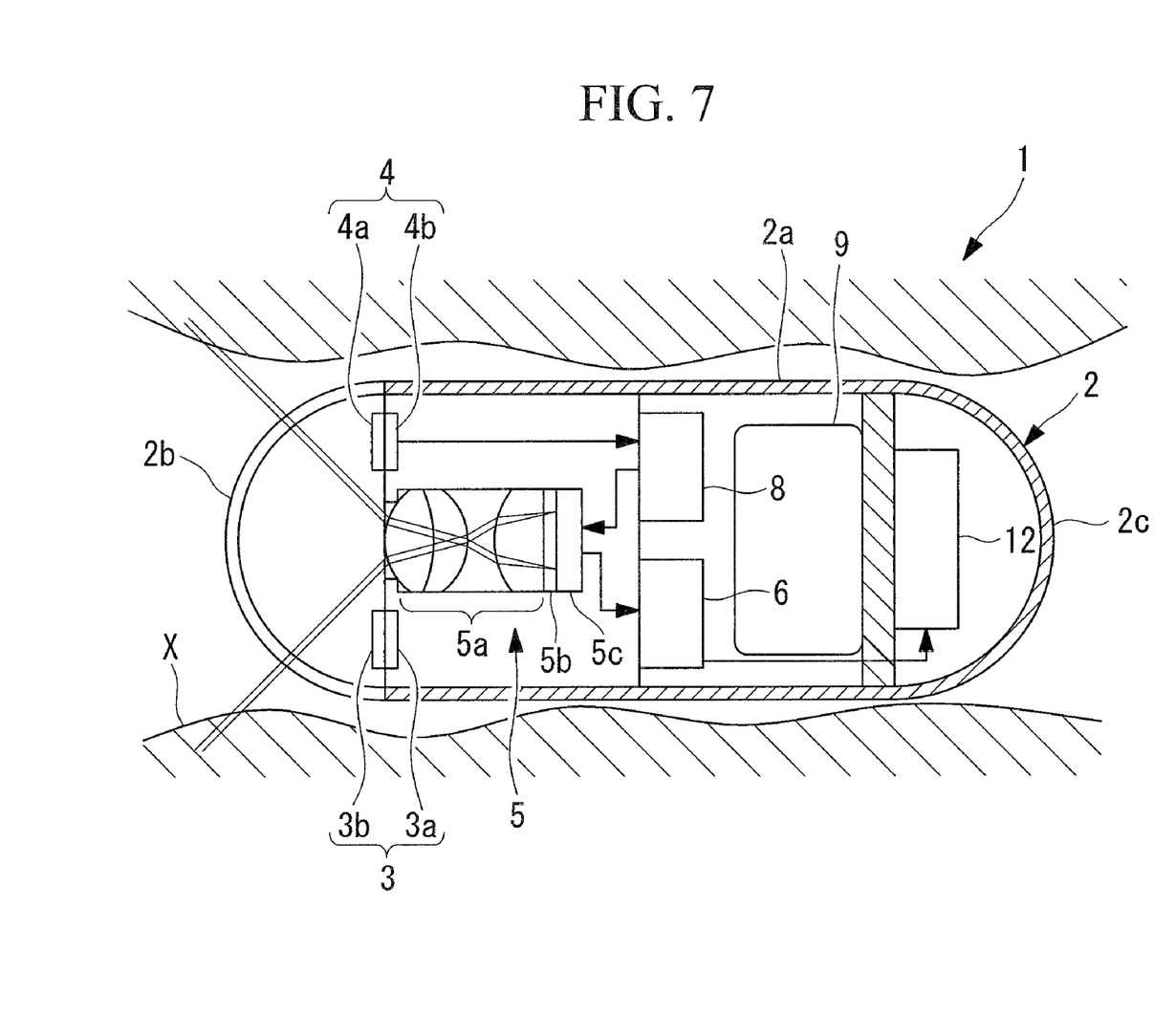
FIG. 7 is a longitudinal sectional view showing a fourth modification of the capsule medical device in FIG. 1.

In addition, although the case where the antenna 7 for wirelessly transmitting the acquired image information outside the casing 2 is provided has been described in this embodiment, as shown in FIG. 7, a memory 12 for storing image information or fluorescence intensity information may instead be provided. Again, in this case, image information or fluorescence intensity information can be stored in the memory 12 in association with examination time to locate the examination site corresponding to the image information or fluorescence intensity information later.

In addition, although the determination is carried out by comparing the information about the detected fluorescence luminance with a predetermined threshold in this embodiment, the threshold may instead be changed.

Figure 8:
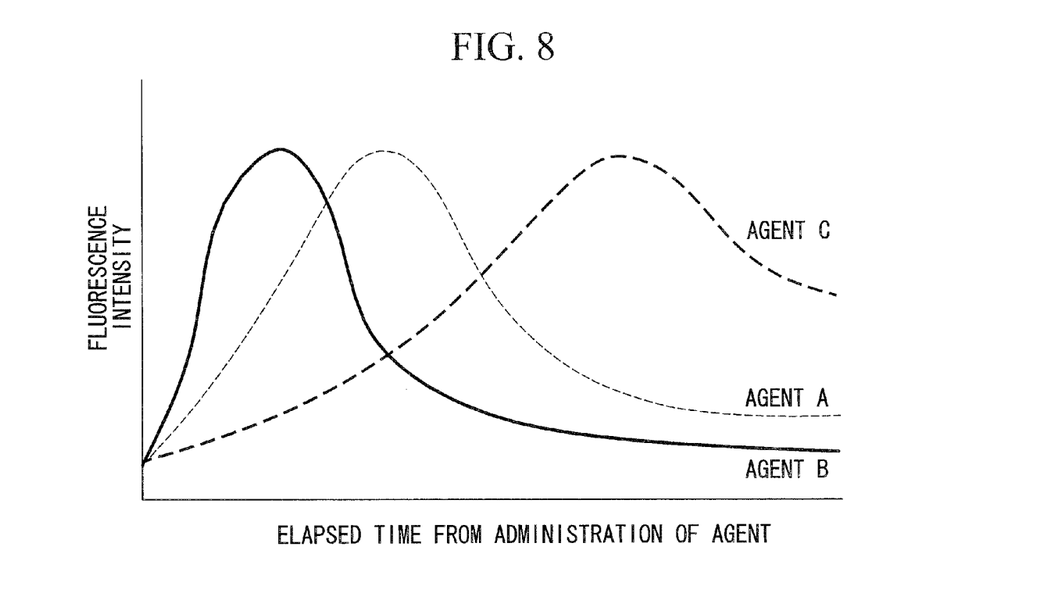
FIG. 8 is a graph showing the relationship between the elapsed time from the administration of a fluorescent agent and the intensity of agent fluorescence.

For example, as shown in FIG. 8, the fluorescence intensity of agent fluorescence varies with the elapsed time from administration of the fluorescent agent. Hence, the fluorescence intensity of fluorescence emitted from the same examination site varies with different elapsed times from administration.

Figure 9:
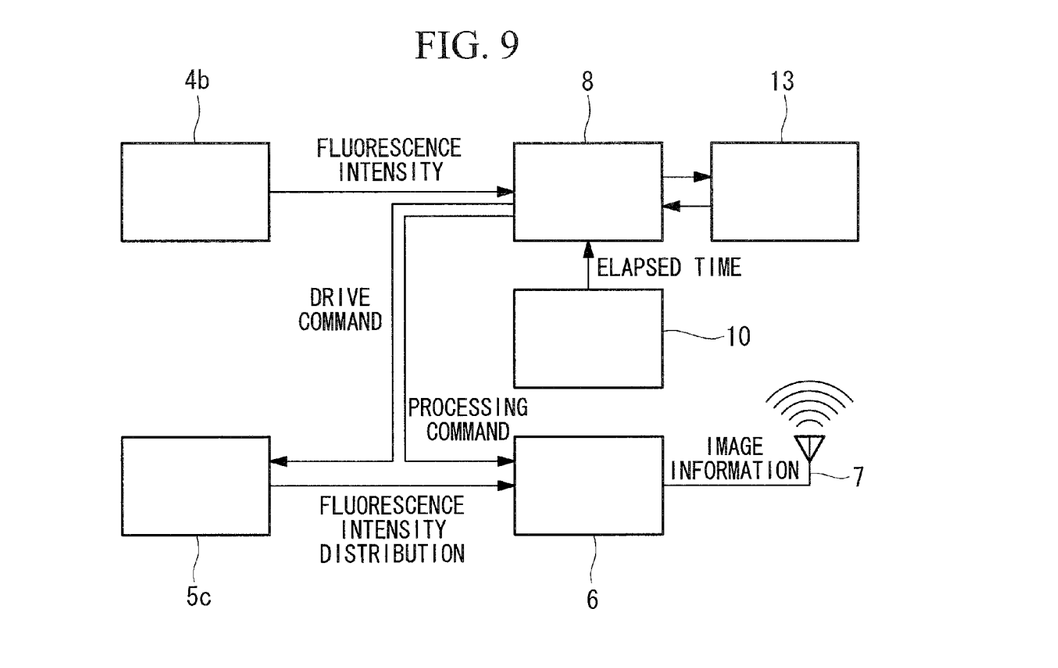
FIG. 9 is a block diagram showing a fifth modification of the capsule medical device in FIG. 1.
Figure 10:
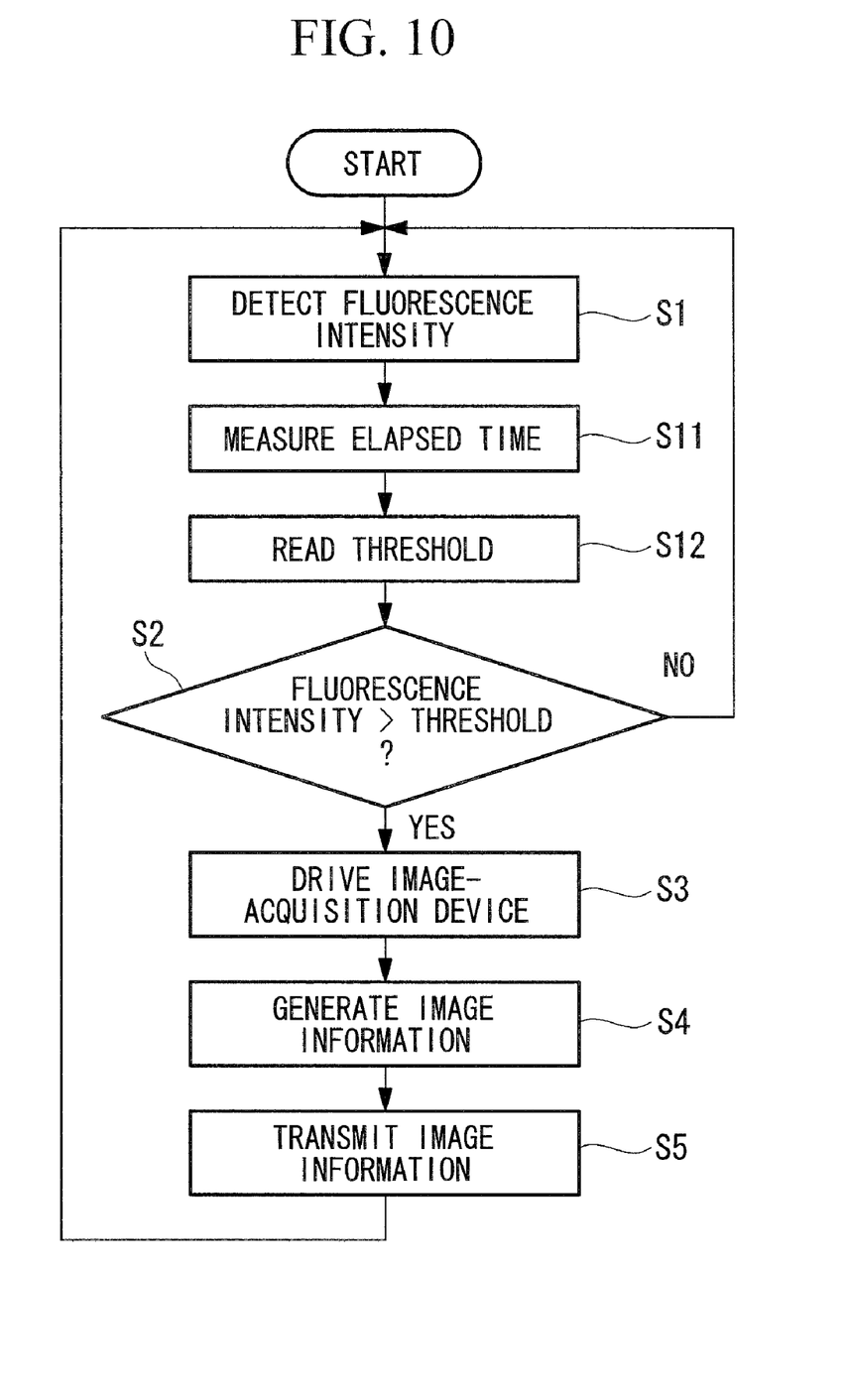
FIG. 10 is a flowchart showing a method for operating the capsule medical device in FIG. 9.

Accordingly, as shown in FIG. 9, the timer 10 that starts counting upon administration of the agent and a threshold table 13 storing thresholds in association with elapsed times may be prepared so that the elapsed time can be measured by the timer 10 to switch the threshold depending on the elapsed time. In this case, as shown in FIG. 10, an elapsed-time measuring step S11 and a threshold-reading step S12 based on the threshold table 13 may be carried out in addition to the processing in FIG. 3 to set an appropriate threshold for determining whether or not to take an image with the image-acquisition device 5c to more accurately take an image of a region that is suspected of being diseased so that images of unnecessary regions can be prevented from being taken.

Figure 11:
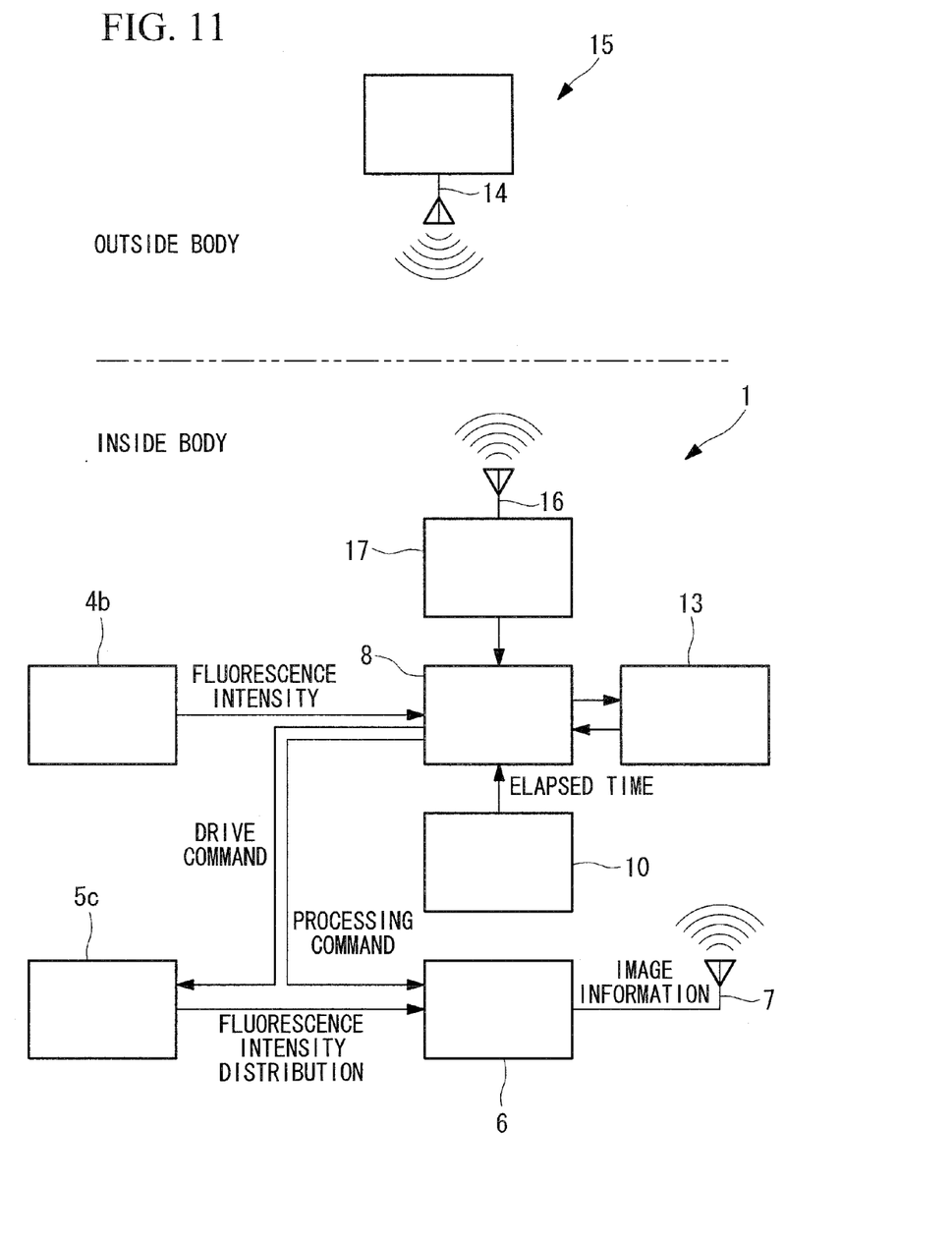
FIG. 11 is a block diagram showing a sixth modification of the capsule medical device in FIG. 1.

As shown in FIG. 8, additionally, the temporal change in the fluorescence intensity of agent fluorescence varies with the type of fluorescent agent. Accordingly, as shown in FIG. 11, it is possible to use a fluorescent-agent selecting device 15 for selecting the type of fluorescent agent outside the patient's body and wirelessly transmitting information about the selected type of fluorescent agent via an antenna 14 and to provide a receiving section 17 for receiving the information, transmitted wirelessly, about the type of fluorescent agent via an antenna 16 in the capsule medical device 1. In addition, the threshold table 13 may store thresholds in association with elapsed times for each type of fluorescent agent.

By doing so, the information about the type of fluorescent agent is selected and wirelessly transmitted via the antenna 14 by operating the fluorescent-agent selecting device 15 disposed outside the patient's body, and the transmitted information about the type of fluorescent agent is received by the receiving section 17 via the antenna 16 in the capsule medical device 1. The control section 8 then reads a threshold stored in the threshold table 13 on the basis of the information, received by the receiving section 17, about the type of fluorescent agent and the elapsed time. This allows appropriate determination as to whether or not to take an image with the image-acquisition device 5c irrespective of the type of fluorescent agent and the elapsed time from administration.

In addition, the fluorescence intensity of agent fluorescence varies with the type of examination site. For example, the behavior of the agent may differ between esophageal cancer (squamous cancer) and colon cancer (adenocarcinoma), and agent fluorescence may also become darker in a low-pH environment such as the stomach. Hence, it can be more accurately determined whether or not to take an image with the image-acquisition device 5c by identifying the examination site (organ) where the capsule medical device 1 is positioned by some method and setting the threshold depending on the particular examination site.

An example of the method for identifying the examination site is a method of identification on the basis of the elapsed time from introduction of the capsule medical device 1 into the body cavity X.

If the examination site is identified on the basis of the elapsed time, individual patients have differences in the relationship between the elapsed time and the examination site; therefore, if the same patient repeatedly undergoes examination, the relationship between the elapsed time and the examination site may be calibrated on the basis of past examination results for each patient. The relationship between the elapsed time and the examination site may also be calibrated on the basis of data such as the patient's weight.

In addition, a pressure sensor may be provided on a sidewall of the casing body 2a to identify the examination site on the basis of the pressure value detected. For example, the examination site can be determined to be a narrow organ such as the esophagus, the small intestine, or the large intestine if the pressure received from the wall surface of the body cavity X is large, and can be determined to be a large organ such as the stomach if the pressure is small.

Figure 12:
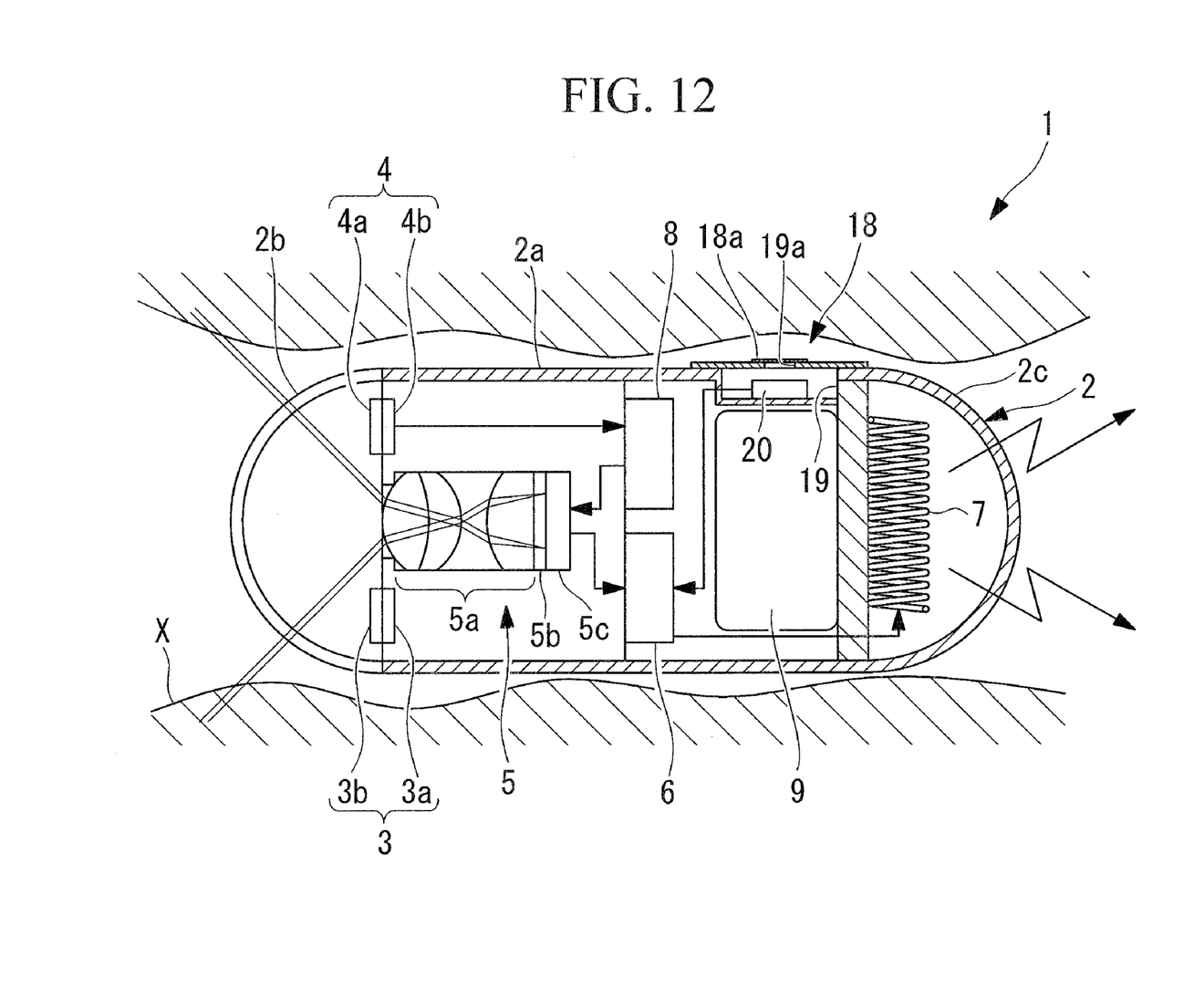
FIG. 12 is a longitudinal sectional view showing a seventh modification of the capsule medical device in FIG. 1.

In addition, as shown in FIG. 12, an enterobacterium sensor 18 may be provided on the sidewall of the casing body 2a. The enterobacterium sensor 18 includes, for example, a pressure chamber 19 set to a predetermined pressure higher than the atmospheric pressure, an azo polymer film 18a that is disposed so as to seal off an opening 19a thereof and that is ruptured by an enzyme secreted by enterobacteria, and a pressure sensor 20 that detects the internal pressure of the pressure chamber 19. A drop in the internal pressure of the pressure chamber 19 due to rupture of the azo polymer film 18a can be detected by the pressure sensor 20 etc. to determine that the examination site has shifted to the large intestine.

In addition, a pH sensor may be provided on the casing body to identify the examination site on the basis of the pH value detected. In addition, the threshold table 13 may store thresholds in association with elapsed times for each examination site.

For example, it can be determined on the basis of the output of the pH sensor that the examination site has shifted to the stomach because the stomach is lower in pH value than other organs. The determination threshold can be correspondingly set to accurately determine whether or not to take an image with the image-acquisition device 5c.

In addition, the timer 10, the pressure sensor 20, the enterobacterium sensor 18, and the pH sensor may be used in any combination.

Figure 13:
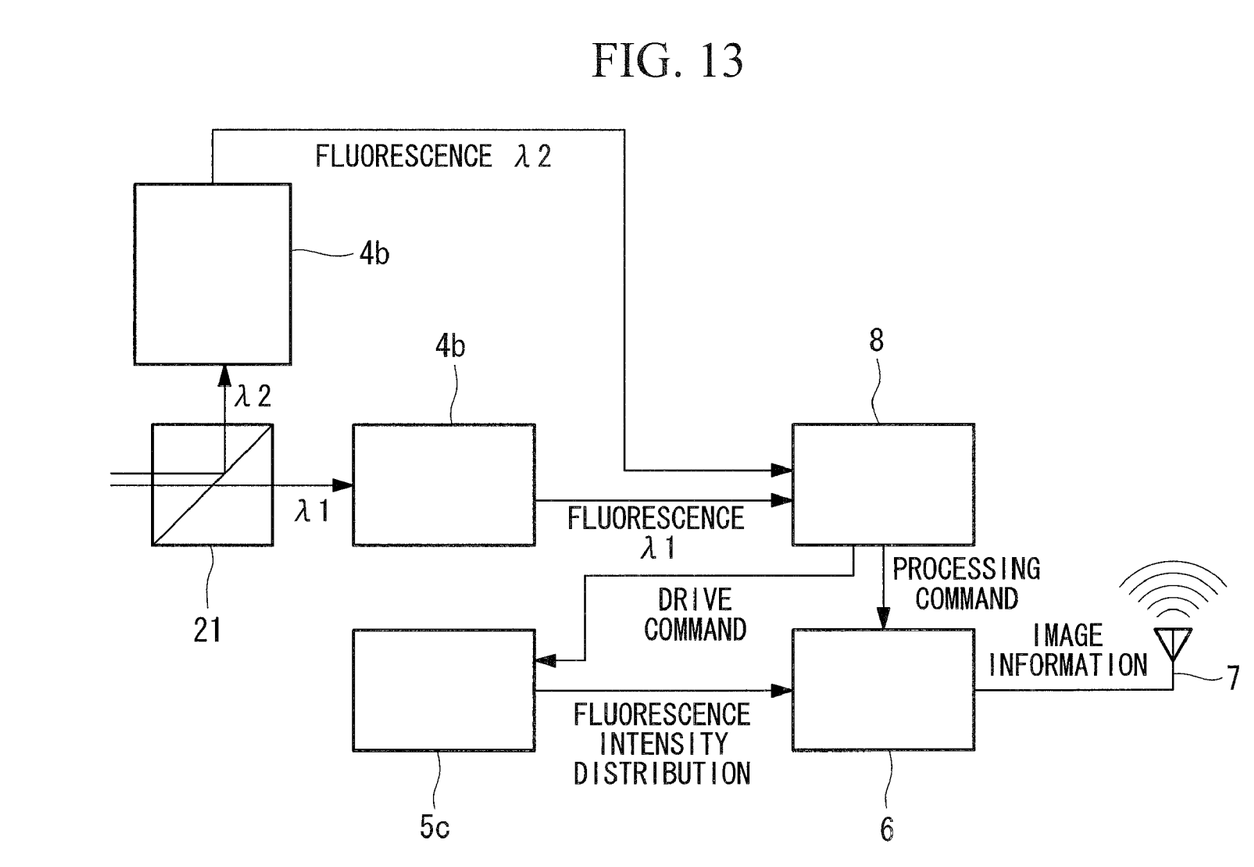
FIG. 13 is a block diagram showing an eighth modification of the capsule medical device in FIG. 1.
Figure 14:
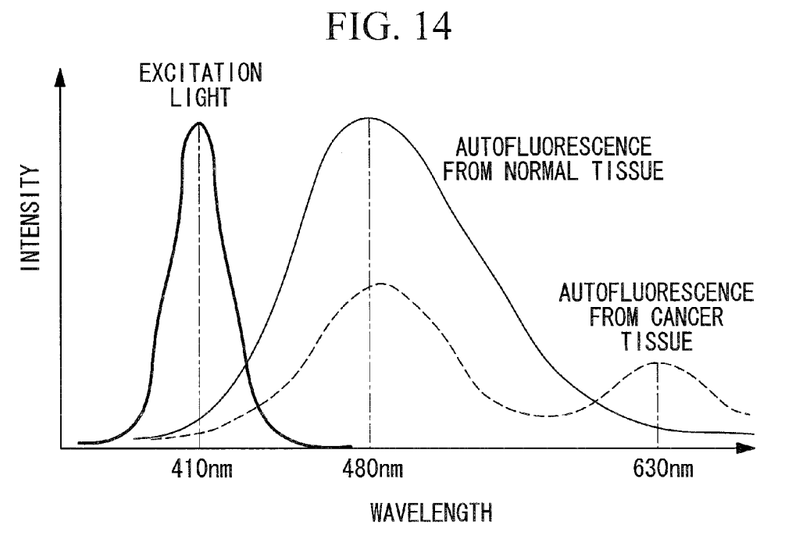
FIG. 14 is a graph showing an example of a determination method for the capsule medical device in FIG. 13.

In addition, although the photodetector 4b is used to detect fluorescence intensity in this embodiment, as shown in FIG. 13, a dichroic mirror 21 may instead be used to split fluorescence into wavelengths $\lambda 1$ and $\lambda 2$ for detection of the fluorescence intensities at the wavelengths $\lambda 1$ and $\lambda 2$. By doing so, as shown in FIG. 14, for excitation with excitation light having a wavelength of 410 nm, it is possible to separately detect the intensity at the wavelength of autofluorescence emitted from blood (about 630 nm) and the intensity at the wavelength of autofluorescence emitted from collagen (about 480 nm). It can therefore be more accurately determined that the presence of cancer cells is strongly suspected in the region under examination if the ratio between these autofluorescence intensities exceeds a predetermined threshold.

Figure 15:
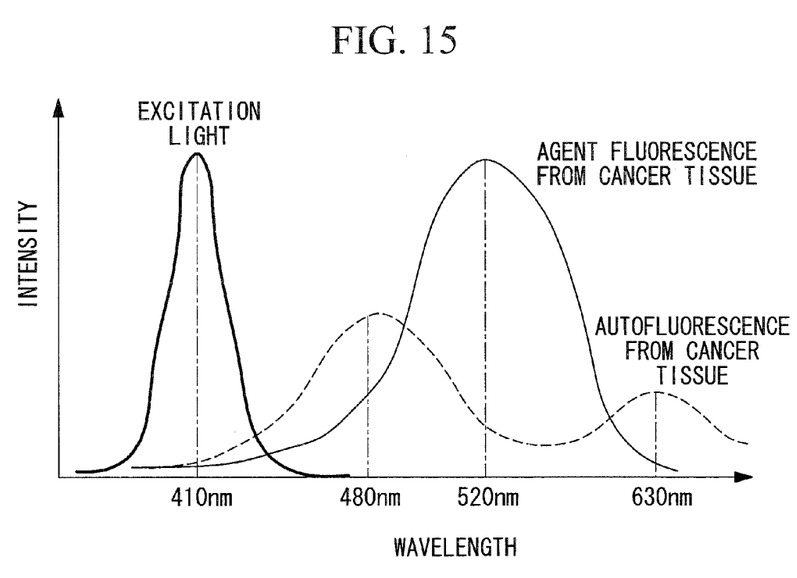
FIG. 15 is a graph showing another determination method for the capsule medical device in FIG. 13.

In addition, as shown FIG. 15, for excitation with excitation light having a wavelength of 410 nm, it is possible to separately detect the fluorescence intensity of a fluorescent agent such as fluorescein, which emits fluorescence having a wavelength of 520 nm, and the intensity at the wavelength of autofluorescence emitted from collagen (about 480 nm), and it can be more accurately determined that the presence of cancer cells is strongly suspected in the region under examination if the ratio between these autofluorescence intensities exceeds a predetermined threshold.

In addition, although the capsule medical device 1 according to this embodiment includes a device for identifying the examination site where the capsule medical device 1 is positioned, for example, the timer 10, the pressure sensor 20, or the pH sensor, a capsule medical device system including an external device (not shown) for locating the capsule medical device 1 outside the patient's body may instead be used. The external device can be exemplified by an X-ray device or electromagnetic induction device that identifies the examination site and that transmits information about it, or the corresponding threshold, to the capsule medical device 1.

What is claimed is:

1. A capsule medical device comprising:
   a casing having a capsule shape;
   a light-detecting section, disposed in the casing, for detecting information about the intensity of light from outside the casing;
   an information-acquiring section for acquiring examination site information from an examination site positioned outside the casing;
   a determination section for determining whether or not to acquire, store, or transmit, to the outside, the examination site information acquired by the information-acquiring section on the basis of the information about the intensity of the light detected by the light-detecting section;
   an examination-site identifying section for identifying the examination site; and
   a threshold-changing section for changing a predetermined threshold depending on the type of examination site identified by the examination-site identifying section,
   wherein the determination section determines that the examination site information is to be acquired, stored, or transmitted to the outside if the information about the intensity of the light detected by the light-detecting section exceeds the predetermined threshold.

2. The capsule medical device according to claim 1, wherein the examination site information is image information from the examination site positioned outside the casing.

3. The capsule medical device according to claim 1, wherein the examination site information is brightness information from the examination site positioned outside the casing.

4. The capsule medical device according to claim 1, wherein
the examination-site identifying section includes an examination-time measuring section for measuring examination time and an examination-site storing section storing types of examination sites in association with the examination time; and
a type of examination site stored in the examination-site storing section is specified on the basis of the examination time measured by the examination-time measuring section.

5. The capsule medical device according to claim 1, wherein
the light-detecting section splits the light from outside the casing to detect information about the intensities of the individual split components; and
the determination section executes the determination on the basis of the ratio of the information about the intensities of the individual split components detected by the light-detecting section.

6. The capsule medical device according to claim 1, wherein the light-detecting section and the information-acquiring section comprise a common light-intensity detecting device.

7. The capsule medical device according to claim 6, wherein
the light-intensity detecting device is an image-acquisition device having a plurality of pixels;
the light-detecting section detects the information about the intensity of the light from at least some of the pixels of the image-acquisition device; and
the information-acquiring section acquires an image of the examination site from at least some of the pixels of the image-acquisition device.

8. The capsule medical device according to claim 7, wherein the determination section executes the determination on the basis of an average value of information about the intensities of pixels having light intensity information exceeding a predetermined threshold and the number of the pixels.

9. The capsule medical device according to one of claim 1, further comprising:
an agent-elapsed-time measuring section for measuring elapsed time from administration of an agent to a patient; and
a threshold-changing section for changing the threshold on the basis of the elapsed time measured by the agent-elapsed-time measuring section.

10. A method for operating a capsule medical device that has a casing having a capsule shape and that is introduced into a patient's body, the method comprising:
a light-intensity detecting step of detecting information about the intensity of light from outside the casing;
a determination step of determining whether or not to acquire examination site information from an examination site positioned outside the casing on the basis of the information about the intensity of the light detected in the light-intensity detecting step;
an information-acquiring step of acquiring the examination site information on the basis of a result of the determination in the determination step;
an examination-site identifying step for identifying the examination site; and
a threshold-changing step for changing a predetermined threshold depending on the type of examination site identified by the examination-site identifying step,
wherein the determination step determines that the examination site information is to be acquired, stored, or transmitted to the outside if the information about the intensity of the light detected by the light-intensity detecting step exceeds the predetermined threshold.

11. A method for operating a capsule medical device that has a casing having a capsule shape and that is introduced into a patient's body, the method comprising:
a light-intensity detecting step of detecting information about the intensity of light from outside the casing;
an information-acquiring step of acquiring examination site information from an examination site positioned outside the casing;
a determination step of determining whether or not to store or transmit, to the outside, the examination site information acquired in the information-acquiring step on the basis of the information about the intensity of the light detected in the light-intensity detecting step;
an information-processing step of storing or transmitting the examination site information on the basis of a result of the determination in the determination step;
an examination-site identifying step for identifying the examination site; and
a threshold-changing step for changing a predetermined threshold depending on the type of examination site identified by the examination-site identifying step,
wherein the determination step determines that the examination site information is to be acquired, stored, or transmitted to the outside if the information about the intensity of the light detected by the light-intensity detecting step exceeds the predetermined threshold.

12. A capsule medical device system comprising a capsule medical device and an external device,
the capsule medical device comprising:
a casing having a capsule shape;
a light-detecting section, disposed in the casing, for detecting information about the intensity of light from outside the casing;
an information-acquiring section for acquiring examination site information from an examination site positioned outside the casing;
a determination section for determining whether or not to acquire, store, or transmit, to the outside, the examination site information acquired by the information-acquiring section on the basis of the information about the intensity of the light detected by the light-detecting section; and
the external device, disposed outside the capsule medical device, comprising
an examination-site identifying section for identifying, from outside the patient's body, the examination site where the capsule medical device is positioned and a transmitting section for transmitting threshold information corresponding to the examination site identified by the examination-site identifying section;
wherein the capsule medical device includes a receiving section for receiving the threshold information transmitted from the transmitting section; and the determination section determines that the examination site information is to be acquired, stored, or transmitted to the outside if the information about the intensity of the light detected by the light-detecting section exceeds a threshold corresponding to the threshold information received by the receiving section.

* * * * *